United States Patent [19]

Nishio et al.

[11] Patent Number: 4,960,755
[45] Date of Patent: Oct. 2, 1990

[54] BU-3608 DERIVATIVES

[75] Inventors: Maki Nishio, Tokyo; Masatoshi Kakushima, Yokohama; Masataka Konishi, Kawasaki; Toshikazu Oki, Yokohama, all of Japan

[73] Assignee: Bristol-Myers Company, New York, N.Y.

[21] Appl. No.: 221,144

[22] Filed: Jul. 19, 1988

[51] Int. Cl.$^5$ .................... A61K 37/10; A61K 31/70; C07H 15/24
[52] U.S. Cl. .......................... 514/8; 514/27; 514/33; 530/322; 536/6.4; 536/18.1; 536/17.2
[58] Field of Search ............ 536/64, 18.1, 17.2; 514/33, 27, 8; 530/322

[56] References Cited

U.S. PATENT DOCUMENTS 4,591,637  5/1986  Acton et al. .................... 536/6.4

OTHER PUBLICATIONS

Konishi et al., Abstract No. 984 of 27th Interscience Conf. on Antimicrobial Agents and Chemotherapy (Oct. 4–7, 1987, NYC).

Primary Examiner—Johnnie R. Brown
Assistant Examiner—Elli Peselev
Attorney, Agent, or Firm—Mollie M. Yang

[57] ABSTRACT

Disclosed herein are N-alkyl derivatives of antibiotics BU-3608, BU-3608 B, C, D and E as well as the corresponding desxylosyl compounds. These novel compounds are useful as antifungal agents.

12 Claims, No Drawings

BU-3608 DERIVATIVES

BACKGROUND OF THE INVENTION

The present invention relates to N-alkyl derivatives of antibiotic BU-3608 complex. These compounds are active as antifungal agents.

The fermentation, and isolation and purification procedures for antibiotics BU-3608, BU-3608 B, and BU-3608 C are described in detail in our co-pending application U.S. Ser. No. 115,273 filed Nov. 2, 1987 now U.S. Pat. No. 4,870,165; the isolation and purification procedures for antibiotics BU-3608 D and BU-3608 E are described in our co-pending application U.S. Ser. No. 203,776, filed June 7, 1988 now pending. These applications are hereby incorporated by reference. The structures of the above mentioned antibiotics are given below as formula Ia–Ie.

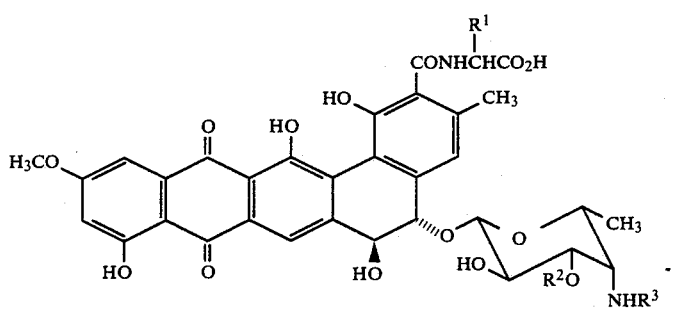

Ia: BU-3608; $R^1=CH_3$; $R^2=$D-xylosyl; $R^3=CH_3$
Ib: BU-3608 B; $R^1=CH_3$; $R^2=H$; $R^3=CH_3$
Ic: BU-3608 C; $R^1=CH_3$; $R^2=$D-xylosyl; $R^3=H$
Id: BU-3608 D; $R^1=H$; $R^2=$D-xylosyl; $R^3=CH_3$
Ie: BU-3608 E; $R^1=H$; $R^2=$D-xylosyl; $R^3=H$.

BU-3608, however, has very limited solubility in water. Thus an object of the present invention provides water soluble derivatives of the various components of the BU-3608 antibiotic complex.

SUMMARY OF THE INVENTION

The present invention provides compounds having the formula II

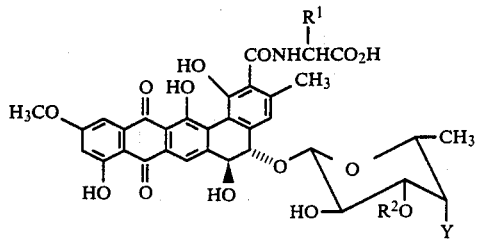

wherein $R^1$ is H, or $R^1$ is methyl in which case the resulting alanyl is D-alanyl; $R^2$ is H or $\beta$-D-xylosyl; Y is $NR^3R^4$ or $N^+R^3R^4R^5$ $X^-$, wherein $R^3$, $R^4$ and $R^5$ are the same or different $C_{1-5}$alkyl; and $X^-$ is an anion; or a pharmaceutically acceptable salt thereof.

$\beta$-D-xylosyl represents the fragment

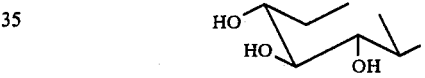

Another aspect of the invention provides the desxylosyl derivatives of BU-3608 C (IIIa), BU-3608 D (IIIb), and BU-3608 E (IIIc), or pharmaceutically acceptable salts thereof.

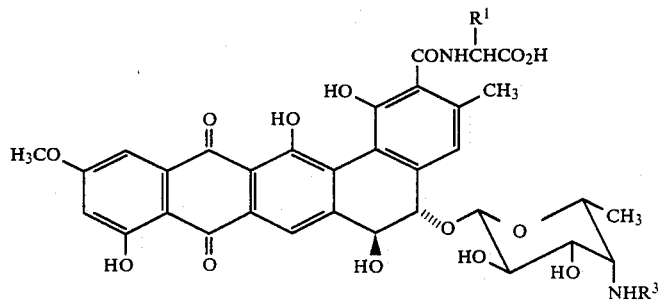

IIIa: $R^1=CH_3$; $R^3=H$
IIIb: $R^1=H$; $R^3=CH_3$
IIIc: $R^1=H$; $R^3=H$.

DETAILED DESCRIPTION OF THE INVENTION

Antibiotics BU-3608, BU-3608 B, BU-3608 C, BU-3608 D, and BU-3608 E are used as starting materials for compounds of the present invention, and may be produced by cultivating an antibiotic producing strain of *Actinomadura hibisca* sp. nov. *Actinomadura hibisca* Strains No. P157-2 and Q278-4 have been deposited with American Type Culture Collection (Rockville, MD) and assigned the accession numbers ATCC 53557 and ATCC 53646, respectively. A mutant strain derived from Strain P157-2 by treatment with N-methyl-N'-nitro-N-nitrosoguanidine (NTG) produces the D and E components in greater amounts than either P157-2 or Q278-4 strains. This mutant strain designated as A2660 has also been deposited with the ATCC and assigned the accession number ATCC 53762.

BU-3608 B is the desxylosyl derivative of BU-3608. BU-3608 B, desxylosyl BU-3608 C, D, and E may be prepared by heating BU-3608, BU-3608 C, D, and E, respectively, in hydrochloric acid for a period sufficient to cleave the xylose group, and adjusting the pH of the solution to precipitate the desired product.

The amino group of BU-3608, BU-3608 C, D, E, or their corresponding desxylosyl derivatives may be alkylated by reductive alkylation which comprises first reacting the antibiotic starting material with an aldehyde or a ketone to form an imine, and subsequently reducing the imine thus formed. The condensation and reduction may be conducted in the same reaction vessel in one step, or in two separate steps. The primary amine group of BU-3608 C, E, or their desxylosyl derivatives may be converted into a tertiary amine having two identical alkyl groups by treatment with at least two equivalents of the carbonyl compound relative to the antibiotic, followed by reduction; or a tertiary amine having two different alkyl substituents may be obtained by using a controlled amount of a first carbonyl reactant to convert the primary amine into a secondary amine which is then reacted with a second different carbonyl compound to give the product tertiary amine.

The carbonyl reactant may be an aldehyde or a ketone having one to five carbon atoms, for example, formaldehyde, acetaldehyde, propionaldehyde, and acetone. Reduction of the imine may be accomplished by using reducing agents such as metal hydrides, for example, sodium borohydride, sodium cyanoborohydride, lithium aluminum hydride. The reaction is carried out in a polar organic solvent or a mixture thereof such as water, acetonitrile, lower alkanols, and dimethyl sulfoxide. The reaction temperature is not particularly restricted and may be from room temperature to about 100° C. In our experience, the alkylation reaction carried out at room temperature is complete within 24 hours. Optimum reaction conditions will of course depend on the nature and reactivity of the particular reactants used.

The amino groups may also be alkylated by reacting with an alkyl halide and quaternary ammonium compounds may be obtained by exhaustively alkylating compounds of formula I, III, or II wherein Y is $NR^3R^4$.

The solubility of the various antibiotics was determined in phosphate-buffered saline (PBS) solutions and the data obtained are shown below. PBS(−) refers to a solution containing for each liter 0.2 g KCl, 0.2 g $KH_2PO_4$, 8 g NaCl, and 1.15 g $Na_2HPO_4$; PBS(+) contains additionally 100 mg $MgCl_2.6H_2O$ and 100 mg $CaCl_2$.

| Compound of | Solubility (μg/ml) | |
|---|---|---|
| Example | PBS(−) | PBS(+) |
| 5 | 330 | 42 |
| 6 | >2100 | 122 |
| 7 | 1800 | >2000 |
| 8 | 3100 | 3 |

-continued

| Compound of | Solubility (μg/ml) | |
|---|---|---|
| Example | PBS(−) | PBS(+) |
| 9 | 73 | 32 |
| 10 | >2700 | — |

In comparison, the solubility of BU-3608 is 16–18 μg/ml and 9–23 μg/ml in PBS(−) and PBS(+) solutions, respectively. Thus compounds of formula II demonstrates increased water solubility compared to BU-3608.

BIOLOGICAL PROPERTIES

Antifungal activities of representative compounds of the present invention were evaluated both in vitro and in vivo. The minimum inhibitory concentrations (MICs) against various fungi were determined by serial agar dilution method using Sabouraud dextrose agar. Thus, approximately 0.003 ml of fungal suspension containing $10^6$ cells/ml was applied to the surface of agar plates containing the test antibiotics. The MIC values recorded after the cultures had been incubated for 44 hours at 28° C. are set forth below in Table I.

TABLE I

| | In vitro Antifungal Activity | | | |
|---|---|---|---|---|
| | MIC (g/ml) | | | |
| Compound of Example | C. albicans | C. neoformans | A. fumigatus | T. mentagrophtes |
| 3 | 3.1 | 1.6 | >100 | >100 |
| 5 | 6.3 | 1.6 | 6.3 | 6.3 |
| 6 | 3.1 | 1.6 | 12.5 | 25 |
| 7 | 6.3 | 1.6 | 12.5 | 25 |
| 8 | 3.1 | 0.8 | 6.3 | 6.3 |
| 9 | 6.3 | 1.6 | 25 | 12.5 |
| 10 | 12.5 | 12.5 | >100 | >50 |

In vivo activity of compounds of the present invention was tested against *Candida albicans* A9540 infection in mice. Test organisms were cultured for 18 hours at 28° C. in YGP medium (yeast extract, glucose, peptone, $K_2HPO_4$, $MgSO_4$) and then suspended in saline. Male ICR mice weighing 20 to 24 g were infected intravenously with about 10 times the median lethal dose of the test fungus. The antibiotic at various dose levels was administered to groups of 5 mice each intravenously just after the fungal infection. The dose that protects 50% of the animals from infection ($PD_{50}$, mg/kg) was calculated from survival rates recorded on the 20th day after the fungal challenge. All control animals died within 7 to 15 days after infection. The $PD_{50}$ for compounds of Examples 5, 7, and 8 are 14 mg/kg (toxic), 11 mg/kg, and 3.5 mg/kg, respectively.

Accordingly, another aspect of the present invention provides a method for treating fungal infections which comprises administering to a host infected with a susceptible fungus an antifungal effective amount of a compound of the present invention. For treatment of fungal infections in animals and human beings, the antibiotics of the present invention may be given in an antifungally effective amount by any accepted routes of administration; these include, but are not limited to, intravenous, intramuscular, oral, intranasal, and for superficial infections, topical administration. Preparations for parenteral administration include sterile aqueous or non-aqueous solutions, suspensions or emulsions. They may also be manufactured in the form of sterile solid compositions which can be dissolved in sterile water, physiological saline, or some other sterile injectable medium immediately before use. Oral formulation may be in the form of tablets, gelatin capsules, powders, lozenges, syrups, and the like. For topical administration, the compound may be incorporated into lotions, ointments, gels, creams, salves, tinctures, and the like. Unit dosage forms may be prepared using methods generally known to those skilled in the art of pharmaceutical formulations.

It will be appreciated that when treating a host infected with a fungus susceptible to the antibiotics of this invention, the actual preferred route of administration and dosage used will be at the discretion of the attending clinician skilled in the treatment of fungal or viral infections, and will vary according to the causative organism, its sensitivity to the antibiotic, severity and site of the infection, and patient characteristics such as age, body weight, rate of excretion, concurrent medications, and general physical condition.

The following examples are illustrative without limiting the scope of the present invention.

EXAMPLE 1

Fermentation of *Actinomadura hibisca* strain P157-2

(a) Agar slant. *Actinomadura hibisca* strain P157-2 was grown on a agar slant consisting of: 0.5% soluble starch (Nichiden Kagaku Co.); 0.5% glucose; 0.1% fish meat extract (Mikuni Kagaku); 0.1% yeast extract (Oriental Yeast Co.); 0.2% NZ case (Sheffield); 0.1% $CaCO_3$; 0.2% NaCl; 1.6% agar. The culture was incubated at 28° C. for 7 days.

(b) Seed culture. A portion of the microbial growth from the slant culture was transferred to a 500 ml Erlenmeyer flask containing 100 ml of vegetative medium of the following composition: 1.0% glucose; 2.0% soluble starch (Nichiden Kagaku Co.); 0.5% NZ amine A (Sheffield); 0.5% yeast extract (Oriental Yeast Co.); and 0.1% $CaCO_3$. The pH of the medium was adjusted to 7.2 before sterilization. The seed culture was incubated at 28° C. for 4 days on a rotary shaker set at 200 rev. per minute.

(c) Flask fermentation. 5 ml of the microbial growth was transferred from the seed culture to a 500 ml Erlenmeyer flask containing 100 ml of sterile production medium of the following composition: 3.0% glucose; 3.0% soybean meal (Nikko Seiyu Co.); 0.5% Pharmamedia (Traders Protein); 0.1% yeast extract (Oriental Yeast Co.); and 0.3% $CaCO_3$. The fermentation was carried out at 28° C. for 5 to 6 days on a rotary shaker. Antibiotic production in the fermentation broth was monitored by broth dilution method using *Candida albicans* A9540 as the indicator organism in Sabouraud dextrose broth; UV assay at 500 nm in 0.01N NaOH—MeOH (1:1) solution was also used. Antibiotic production reached a maximum at 650 µg/ml on day 5.

(d) Tank fermentation. 3 l of the seed culture was used to inoculate 120 l of sterile production medium contained in a 200 l tank fermentor. The composition of the production medium is the same as that used in flask fermentation. The tank was operated at 28° C. with the agitation rate set at 250 rev. per minute and the aeration rate at 120 l per minute. After 96 hrs of fermentation, an antibiotic potency of 500 µg/ml was obtained, and the pH of the broth was 7.9.

EXAMPLE 2

Isolation and Purification of Antibiotics

Detailed description of procedures for the isolation and purification of antibiotics BU-3608, BU-3608 B, and BU-3608 C is given in our co-pending application U.S. Ser. No. 115,273 filed Nov. 2, 1987. Isolation and purification of the D and E components is described in co-pending application Ser. No. 203,776, filed June 7, 1988. These applications are hereby incorporated by reference. The procedure for isolating and purifying the various components of the antibiotic complex is described herein below.

Harvested broth (pH 7.8) was centrifuged and the supernatant was acidified to pH 2.0 with 6N HCl to deposit bio-inactive solid. After the precipitate was removed, the filtrate was adjusted to pH 5.0 with 6N NaOH and the solution was stirred gently for 30 minutes at room temperature. The resultant dark red solid was filtered off and dried in vacuo. This solid was dissolved in a 3:1:4 mixture of n-butanol-methanol-1% NaCl and the mixture was stirred for 30 minutes. The lower aqueous layer was separated, washed again with fresh upper layer, acidified to pH 2.0 with 6N HCl, and then extracted with n-butanol. The n-butanol extract was washed with water, concentrated in vacuo and lyophilized to yield semi-pure BU-3608 hydrochloride. A solution of the solid in n-butanol was shaken with alkaline water (pH 9.0). The aqueous layer was acidified to pH 2.0 and washed with ethyl acetate. Extraction with n-butanol followed by evaporation of the solvent gave a purer sample of BU-3608 HCl. This material was then subjected to reversed phase silica gel chromatography (ODS-60, 350/250 mesh, Yamamura Chemical Lab., column 4.5×90 cm). The sample was dissolved in water and applied on the column which had been equilibrated with a mixture of acetonitrile-0.15% $KH_2PO_4$ (pH 3.5)=17:83 (v/v). The column was washed sequentially with 5 l each of acetonitrile-0.15% $KH_2PO_4$ mixture of the following ratios: 17:83, 18:82, 19:81, 20:80, and then developed with the same solvent mixture of a 22:78 ratio. The eluate was collected in 100 ml fractions which were monitored by the microplate assay using *C. albicans* A9540 and thin-layer chromatography ($SiO_2$, methyl acetate-n-propanol-28% ammonium hydroxide=45:105:60 v/v). The fractions containing the main homogeneous compound were combined and further purified to yield BU-3608.

In the reversed phase silica gel chromatography procedure described above, the fractions eluting before and after the main homogeneous BU-3608 fraction were pooled. The combined eluate was desalted using HP-20 resin to afford a BU-3608 B-containing solid and a BU-3608 C-containing solid. The BU-3608 B-containing solid was dissolved in water and applied on a column of ODS-60 (Yamamura Chem. Lab. 8.0×90 cm) which had been thoroughly washed with a 22:78 (v/v) mixture of acetonitrile-0.15% $KH_2PO_4$ (pH 3.5). This same solvent mixture was used to elute the loaded column and fractions were collected and examined by HPLC. Fractions containing BU-3608 B were pooled, concentrated in vacuo, and desalted by HP-20 resin chromatography to yield impure BU-3608, pure BU-3608, and BU-3608 B. BU-3608 B was further purified by preparative HPLC using a Microsorb Short One $C_{18}$ column (4.6 mm I.D.×100 mm, 3 µm, Rainin Instrument Co.), and elution was carried out using 29:71 (v/v) mixture of acetonitrile-0.15% $KH_2PO_4$ (pH 3.5). The BU-3608 C-containing solid was purified in a similar fashion using the ODS column with elution by a 21:79 (v/v) mixture of acetonitrile-0.15% $KH_2PO_4$ (pH 3.5). HPLC was used to monitor the eluate and fractions containing BU-3608 C were pooled and concentrated in vacuo. The resultant aqueous solution was desalted by HP-20 chromatography to yield nearly pure BU-3608 C, and nearly pure BU-3608.

In the reversed phase silica gel chromatography procedure described above, fractions eluting before BU-3608 C were separately collected and pooled. The pooled pale orange-colored fractions were desalted using Diaion HP-20 chromatography. The solid thus obtained was relatively enriched in the D and E components but still contained a large amount of the C component. The pooled solids was charged on a column of reversed phase silica gel (ODS-60, Yamamura Chem. Lab., Φ 8.0×90 cm), and eluted with a 21:79 mixture of acetonitrile-0.15% $KH_2PO_4$ (pH 3.5). The eluate was examined by HPLC using a Microsorb Short One $C_{18}$ column (Rainin Instrument Co., 4.6 mm I.D.×100 mm, 3 μm), a 7:17 mixture of acetonitrile-0.15% $KH_2PO_4$ (pH 3.5) as the mobile phase at a flow rate of 1.2 ml/min., and UV absorption at 254 nm for detection. BU-3608 E eluted first followed by BU-3608 D. Fractions containing BU-3608 E were pooled, concentrated in vacuo and desalted by HP-20 chromatography to yield nearly homogeneou BU-3608 E HCl. An aqueous solution of BU-3608 E HCl was adjusted to pH 5.0 with 0.1N NaOH to deposit pure BU-3608 E as the zwitterion. In a similar fashion, BU-3608 D as the zwitterion was obtained.

EXAMPLE 3

Preparation of desxylosyl BU-3608 E (IIIc)

A solution of BU-3608 E hydrochloride (97 mg) in 2N HCl (12 ml) was heated at 115° C. for 70 minutes in a sealed tube. The resulting solution was adjusted to pH 5.5 by addition of 1N NaOH, and then centrifuged. The solid thus obtained was washed with isopropanol and acetone to give 87 mg of desxylosyl BU-3608 E. M.p.: 205°–209° C. (dec.), UV $\lambda_{max}^{0.01N\ NaOH}$ nm(ε): 235.2 (23600), 319.2 (11100), 498.4 (10800).

EXAMPLE 4

Preparation of desxylosyl BU-3608 C (IIIa)

The procedure described in Example 3 is repeated using BU-3608 C hydrochloride to provide the title compound. M.P. 208°–215° C. (dec.).

EXAMPLE 5

Preparation of N-methyl BU-3608 B (II; $R^2$=H; $R^1$=$R^3$=$R^4$=$CH_3$)

A mixture of BU-3608 (540 mg) in 2N HCl (60 ml) was heated at 115° C. in a sealed tube for 70 minutes and cooled. The resulting solid material was collected by centrifugation (3000 rpm), suspended in $H_2O$ and the pH was adjusted to 11.7 by adding 6N NaOH. The solution (60 ml) was added to acetone (300 ml) and the resulting BU-3608 B as a solid was collected. The solid was dissolved in $H_2O$ (20 ml) and 1N HCl was added to adjust the pH to 8.3 and then diluted with $CH_3CN$ (20 ml). Aqueous HCHO (37%, 0.8 ml) and $NaBH_3CN$ (120 mg) were sequentially added to the solution at room temperature and the solution was stirred at room temperature for 15 hours. The solvent was removed in vacuo and the aqueous residue was added dropwise to stirred acetone. The resulting solid was washed with acetone and dried to give 440 mg of N-methyl BU-3608 B sodium salt. A part of this salt (50 mg) was dissolved in $H_2O$ and the solution was adjusted to pH 6.0 with 1N HCl. The resulting solid was washed with $H_2O$ and lyophilized to give 33 mg of zwitterionic form. M.p.: 211°–215° C. (dec.), UV $\lambda_{max}^{0.01N\ NaOH-MeOH}$ nm (ε): 240.8 (29700), 319.2 (13400), 499.2 (13100).

EXAMPLE 6

Preparation of N,N-dimethyl desxylosyl BU-3608 E (II; $R^1$=$R^2$=H; $R^3$=$R^4$=$CH_3$)

A solution of desxylosyl BU-3608 E (52.9 mg) in $H_2O$ (5 ml, pH 8.4) was diluted with $CH_3CN$ (5 ml). Aqueous HCHO (0.2 ml) and $NaBH_3CN$ (30 mg) were added sequentially at room temperature to the solution and the resulting solution was stirred at room temperature for 14 hours. The solvent was removed in vacuo and the aqueous residue (pH 11.3) was added dropwise to stirred acetone. The precipitate collected was dissolved in $H_2O$ and adjusted to pH 5.5 to give a solid which was washed with $H_2O$, isopropanol and acetone sequentially and dried to give 28.7 mg of N,N-dimethyldesxylosyl BU-3608 E. M.p.: 205°–208° C. (dec.), UV $\lambda_{max}^{0.01N\ NaOH}$ nm (ε): 232.8 (34000), 319.2 (15700), 497.6 (14900).

EXAMPLE 7

Preparation of N,N-dimethyl BU-3608 E (II; $R^1$=H; $R^2$=D-xylosyl; $R^3$=$R^4$=$CH_3$)

To a solution of BU-3608 E (485 mg) in a mixture of $H_2O$ (40 ml) and $CH_3CN$ (40 ml) at pH 8.0 were added sequentially aq. HCHO (37%, 1.6 ml) and $NaBH_3CN$ (240 mg) at room temperature. The solution was stirred at room temperature for 15 hours and the solvent was removed in vacuo. The residue was dissolved in $H_2O$ (50 ml), adjusted to pH 11.0 and added dropwise to stirred acetone (300 ml). The resulting precipitate was collected, dissolved in $H_2O$ and adjusted to pH 2.0 with 6N HCl. The solution was desalted by passage over HP-20. The solution containing the product was adjusted to pH 5.5 to deposit a solid which was collected, washed with $H_2O$ and acetone, and dried to afford 364 mg of N,N-dimethyl BU-3608 E. M.p.: 214°–218° C. (dec.), UV $\lambda_{max}^{0.01N\ NaOH}$ nm (ε): 233.6 (32900), 319.2 (15500), 497.6 (15100).

Anal. Calcd. for $C_{40}H_{44}N_2O_{18}\cdot 1.5H_2O$: C, 55.36; H, 5.46; N, 3.23. Found: C, 55.26; H, 5.45; N, 3.19.

EXAMPLE 8

Preparation of N-methyl BU-3608 (II; $R^1$=$R^3$=$R^4$=$CH_3$; $R^2$=D-xylosyl)

To a stirred solution of BU-3608 sodium salt (550 mg) in 50% aqueous $CH_3CN$ (55 ml) were added HCHO (37%, 0.75 ml) and $NaBH_3CN$ (150 mg) and the mixture was stirred for 18 hours at room temperature. After concentration, the aqueous concentrate was diluted (200 ml), acidified to pH 3.0 and subjected to column chromatography on HP-20 (300 ml). Upon washing with water and subsequent eluting with 60% aqueous acetone (pH 3.0), the red-colored eluate was concentrated in vacuo and adjusted to pH 5.5 to precipitate N-methyl-BU-3608 which was collected by filtration (425 mg). M.p. 190°–195° C. (dec.); IR(KBr) cm$^{-1}$ 3400, 1605, 1450, 1295; UV $\lambda_{max}^{50\%MeOH}$ nm (ε) 220 (33,700), 278 (26,800), 488 (11,400); SI-MS m/z 855 $(M+H)^+$.

EXAMPLE 9

Preparation of N-propyl BU-3608 (II; $R^1=R^3=CH_3$; $R^2$=D-xylosyl; $R^4=(CH_2)_2CH_3$)

The general procedure of Example 8 was followed using BU-3608 sodium salt (200 mg), propionaldehyde (1 ml) and NaBH$_3$CN (200 mg) to give N-propyl BU-3608 (127 mg). M.p. 187°–192° C. (dec.); IR(KBr) cm$^{-1}$ 3380, 1605, 1450, 1295, 1255; UV $\lambda_{max}^{50\%MeOH}$ nm ($\epsilon$): 223 (33,000), 278 (27,500), 488 (11,700); SI-MS m/z 883 (M+H)$^+$.

EXAMPLE 10

Preparation of quaternary ammonium derivative of BU-3608 (II; Y=N(CH$_3$)$_3$Cl)

BU-3608 sodium salt (140 mg) was treated with methyl iodide (1.5 ml) and potassium bicarbonate (200 mg) in dimethyl sulfoxide (5 ml) and methanol (20 ml) at room temperature for 43 hours. The mixture was concentrated, diluted with 0.5N NaOH (20 ml) and kept for 30 minutes at 70° C. The solution was adjusted to pH 3.0 and subjected to a HP-20 column (150 ml) for desalting. The eluate containing the title compound was evaporated to yield crude solid of quaternary ammonium derivative of BU-3608 (144 mg). The crude solid was purified by reversed phase silica gel chromatography ($\Phi$2.0×45 cm) with CH$_3$CN-0.15% KH$_2$PO$_4$, pH 3.0 (20:80) elution. Eluate was examined by HPLC and the fractions containing pure quaternary derivative were pooled and desalted by HP-20 chromatography (150 ml) to give pure title compound (71 mg). MP 205°–210° C. (dec.); IR(KBr) cm$^{-1}$ 3400, 1620, 1600, 1440, 1255; UV $\lambda_{max}^{50\%MeOH}$ nm ($\epsilon$) 276 (22,300), 498 (9,800); SI-MS m/z 869 (M$^+$); Molecular formula C$_{42}$H$_{49}$N$_2$O$_{18}$Cl.

EXAMPLE 11

Preparation of desxylosyl BU-3608 D (IIIb)

The procedure described in Example 3 was repeated using BU-3608 D hydrochloride to provide the title compound. M.P. 205°–211° C. (dec.).

We claim:

1. A compound having the formula

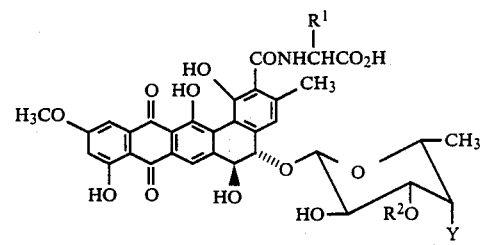

wherein
- $R^1$ is H, or $R^1$ is methyl and the resulting alanyl is D-alanyl;
- $R^2$ is H or $\beta$-D-xylosyl; and
- Y is NR$^3$R$^4$ or $^+$NR$^3$R$^4$R$^5$ X$^-$; wherein R$^3$, R$^4$ and R$^5$, are the same or different C$_{1-5}$alkyl; and X$^-$ is a chloride ion; or a pharmaceutically acceptable salt thereof.

2. The compound of claim 1 having the formula

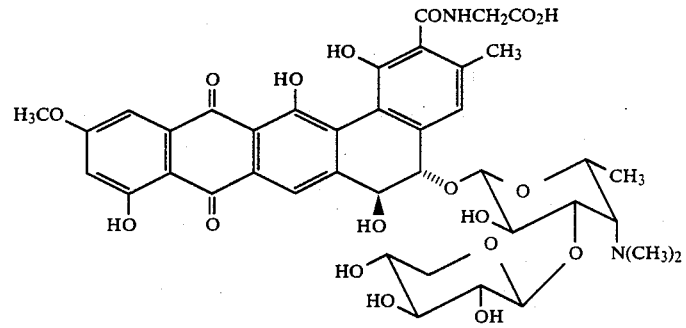

or a pharmaceutically acceptable salt thereof.

3. The compound of claim 1 having the formula

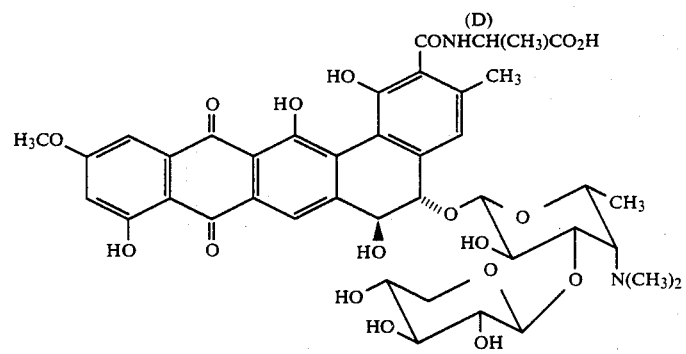

or a pharmaceutically acceptable salt thereof.

4. The compound of claim 1 having the formula

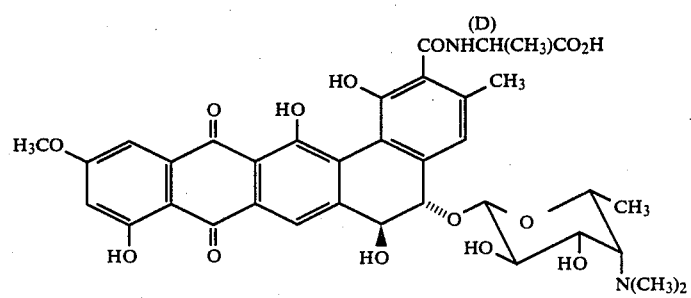
or a pharmaceutically acceptable salt thereof.
5. The compound of claim 1 having the formula
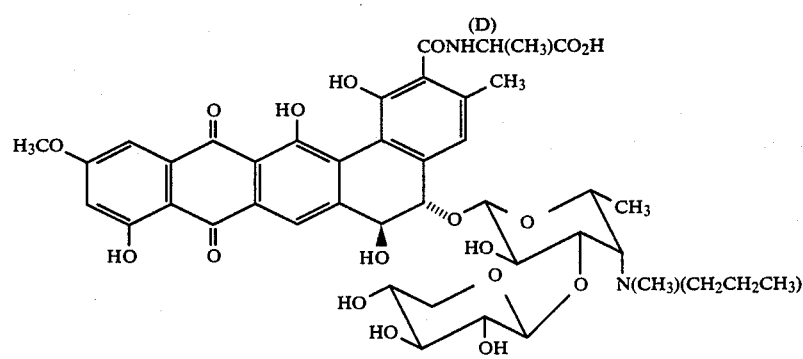
6. The compound of claim 1 having the formula
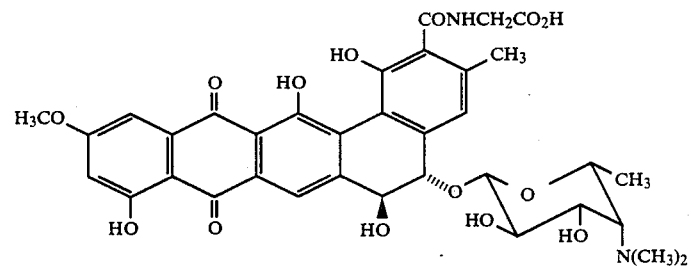
or a pharmaceutically acceptable salt thereof.
7. The compound of claim 1 having the formula
8. A compound having the formula
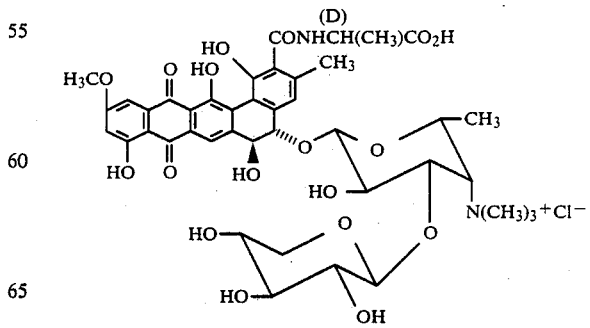

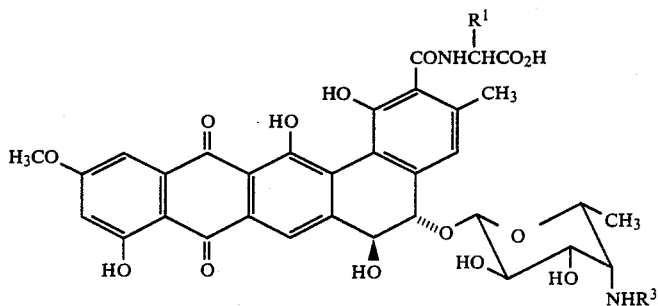

wherein
R[1] is H and R[3] is H or methyl; or a pharmaceutically acceptable salt thereof.

9. The compound of claim 8 wherein R[1] and R[3] are both H; or a pharmaceutically acceptable salt thereof.

10. The compound of claim 8 wherein R[1] is H and R[3] is methyl; or a pharmaceutically acceptable salt thereof.

11. A method for treating fungal infection in a mammalian host which comprises administering to said host an antifungal amount of a compound of claim 1 or claim 7.

12. A pharmaceutical composition which comprises an antifungal effective dose of a compound of claim 1 or claim 7 and a pharmaceutically acceptable carrier.

* * * * *